US010961556B2

(12) United States Patent
Ley et al.

(10) Patent No.: US 10,961,556 B2
(45) Date of Patent: Mar. 30, 2021

(54) METHOD FOR REDUCING AMMONIUM AND LACTATE PRODUCTION IN CHO CELLS

(71) Applicant: DANMARKS TEKNISKE UNIVERSITET, Kgs. Lyngby (DK)

(72) Inventors: Daniel Ley, Kgs. Lyngby (DK); Mikael Rørdam Andersen, Farum (DK); Helene Faustrup Kildegaard, Værløse (DK)

(73) Assignee: DANMARKS TEKNISKE UNIVERSITET, Lyngby (DK)

( * ) Notice: Subject to any disclaimer, the term of this patent is extended or adjusted under 35 U.S.C. 154(b) by 0 days.

(21) Appl. No.: 16/325,583

(22) PCT Filed: Aug. 15, 2017

(86) PCT No.: PCT/EP2017/070682
§ 371 (c)(1),
(2) Date: Feb. 14, 2019

(87) PCT Pub. No.: WO2018/033542
PCT Pub. Date: Feb. 22, 2018

(65) Prior Publication Data
US 2019/0203249 A1 Jul. 4, 2019

(30) Foreign Application Priority Data
Aug. 15, 2016 (EP) .................................. 16184179

(51) Int. Cl.
C12P 21/02 (2006.01)
C12N 5/071 (2010.01)
C12N 15/52 (2006.01)
C12N 9/02 (2006.01)

(52) U.S. Cl.
CPC ............ C12P 21/02 (2013.01); C12N 5/0682 (2013.01); C12N 15/52 (2013.01); C12Y 113/11027 (2013.01); C12N 9/0069 (2013.01)

(58) Field of Classification Search
None
See application file for complete search history.

(56) References Cited

U.S. PATENT DOCUMENTS

2010/0319078 A1  12/2010  McKnight et al.

FOREIGN PATENT DOCUMENTS

| WO | WO 2000/26357 A2 | 5/2000 |
| WO | WO 2002/101013 A2 | 12/2002 |
| WO | WO 2004/046348 A1 | 6/2004 |
| WO | WO 2008/124724 A1 | 10/2008 |
| WO | WO 2009/086215 A2 | 7/2009 |
| WO | WO 2012/082409 A1 | 6/2012 |
| WO | WO 2012/135389 A2 | 10/2012 |
| WO | WO 2013/032918 A1 | 3/2013 |
| WO | WO 2015/048577 A2 | 4/2015 |

OTHER PUBLICATIONS

Ji and Obata, "Development of the GABA system in organotypic culture of hippocampal and cerebellar slices from a 67-kDa isoform of glutamic acid decarboxylase (GAD67)-deficient mice", Neuroscience Research 33: 233-237. (Year: 1999).*

Makinae et al., "Structure of the mouse glutamate decarboxylase 65 gene and its promoter: preferential expression of its promoter in the GABAergic neurons of transgenic mice", Journal of Neurochemistry 75: 1429-1437. (Year: 2000).*

Pereira et al., "BCAT1 and BCAT2 disruption in CHO cells has cell line-dependent effects", Journal of Biotechnology 306: 24-31. (Year: 2019).*

Ley et al., "Multi-omic profiling of EPO-producing Chinese hamster ovary cell panel reveals metabolic adaptation to heterologous protein production", Biotechnology and Bioengineering, Nov. 2015, pp. 2373-2387, vol. 112, No. 11, Biotechnology and Bioengineering.

Brodsky et al., "Glycosylation-related genes in NS0 cells are insensitive to moderately elevated ammonium concentrations", Journal of Biotechnology, 187 (2014) pp. 78-86.

Gray et al., "One-step generation of triple knockout CHO cell lines using CRISPR/Cas9 and fluorescent enrichment", Biotechnology Journal, 2015, 10(9):1446-1456.

Hallen et al., "Lysine metabolism in mammalian brain: an update on the importance of recent discoveries", Amino Acids, Dec. 2013, p. 1-36, 45(6).

Hammond et al., 2012. "Chinese hamster genome database: An online resource for the cho community at www. CHOgenome.org," Biotechnology and Bioengineering, Jun. 2012, pp. 1353-1356 vol. 109, No. 6.

Kanehisa et al, "KEGG: Kyoto Encyclopedia of Genes and Genomes", Nucleic Acids Research, 2000, pp. 27-30, vol. 28 No. 1.

Lao et al., "Effects of ammonium and lactate on growth and metabolism of a recombinant Chinese hamster ovary cell culture", Biotechnology Progress, 1997, pp. 688-691, Vo. 13, No. 5.

Lund et al., "Network reconstruction of the mouse secretory pathway applied on CHO cell transcriptome data", BMC Syst Biol., 2017, pp. 1-17, 11:37.

Nicolae et al., "Non-stationary $^{13}$C metabolic flux analysis of Chinese hamster ovary cells in batch culture using extracellular labeling highlights metabolic reversibility and compartmentation", BMC Systems Biology, 2014, pp. 1-15, 8:50.

(Continued)

Primary Examiner — Anand U Desai
(74) Attorney, Agent, or Firm — Marshall, Gerstein & Borun LLP

(57) ABSTRACT

The present invention relates to modified producer cells for improved production of therapeutic proteins. Specifically, the inventors have found that removing genes involved in amino acid catabolism in Chinese Hamster Ovary (CHO) cells improves the cell growth and viability and likely also the yield of a recombinant therapeutic protein produced by the cells.

14 Claims, 1 Drawing Sheet

(56) References Cited

OTHER PUBLICATIONS

Pan et al., "Adaptation of Phenylanaline and Tyrosine Catabolic Pathway to Hibernation in Bats", PLoS ONE, Apr. 2013, 15 pages, 8(4): e62039. doi:10.1371/journal.pone.0062039.

Ronda et al., "Accelerating Genome Editing in CHO Cells Using CRISPR Cas9 and CRISP$_y$, a Web-Based Target Finding Tool", Biotechnology and Bioengineering, Aug. 2014, pp. 1604-1616, vol. 111, No. 8.

Templeton et al, "The impact of anti-apoptotic gene Bcl-2 expression on CHO central metabolism", Metabolic Engineering, 2014, p. 92-102, 25.

Gary Walsh, 2014 "Biopharmaceutical benchmarks 2014", Nature Biotechnology, Oct. 2014, pp. 992-1000, vol. 32, No. 10.

Zhou et al., "Decreasing lactate level and increasing antibody production in Chinese hamster Ovary cells (CHO) by reducing the expression of lactate dehydrogenase and pyruvate dehydrogenase kinases", Journal of Biotechnology, 2011, pp. 27-34, vol. 153.

Doolan et al., "Microarray and Proteomics Expression Profiling Identifies Several Candidates, Including the Valosin-Containing Protein (VCP), Involved in Regulating High Cellular Growth Rate in Production CHO Cell Lines", Biotechnology and Bioengineering, May 1, 2010, pp. 42-56, vol. 106, No. 1, Wiley Periodicals, Inc.

Rodrigues et al., "Increased Titer and Reduced Lactate Accumulation in Recombinant Retrovirus Production Through the Down-Regulation of HIF1 and PDK", Biotechnology and Bioengineering, Jan. 2016, pp. 150-162, vol. 113, No. 1.

Hassell et al., "Growth Inhibition in Animal Cell Culture: The Effect of Lactate and Ammonia", Applied Biochemistry and Biotechnology, 1991, pp. 29-41, vol. 30, No. 1.

Fischer et al., "The art of CHO cell engineering: A comprehensive retrospect and future perspectives", Biotechnology Advances, pp. 1878-1896, 2015, vol. 33, No. 8, pp. 1878-1896.

Graham R. Moran, "4-Hydroxyphenylpyruvate dioxygenase", Archives of Biochemistry and Biophysics, Academic Press, 2005 pp. 117-128, vol. 433, No. 1.

Kash et al., "Epilepsy in mice deficient in the 65-kDa isoform of glutamic acid decarboxylase", Proceedings National Academy of Sciences PNAS, 1997, pp. 14060-14065, vol. 94, No. 25.

Erlander et al., "Two Genes Encode Distinct Glutamate Decarboxylases", Neuron Cell Press, Jul. 1991, vol. 7, pp. 91-100, No. 1.

\* cited by examiner

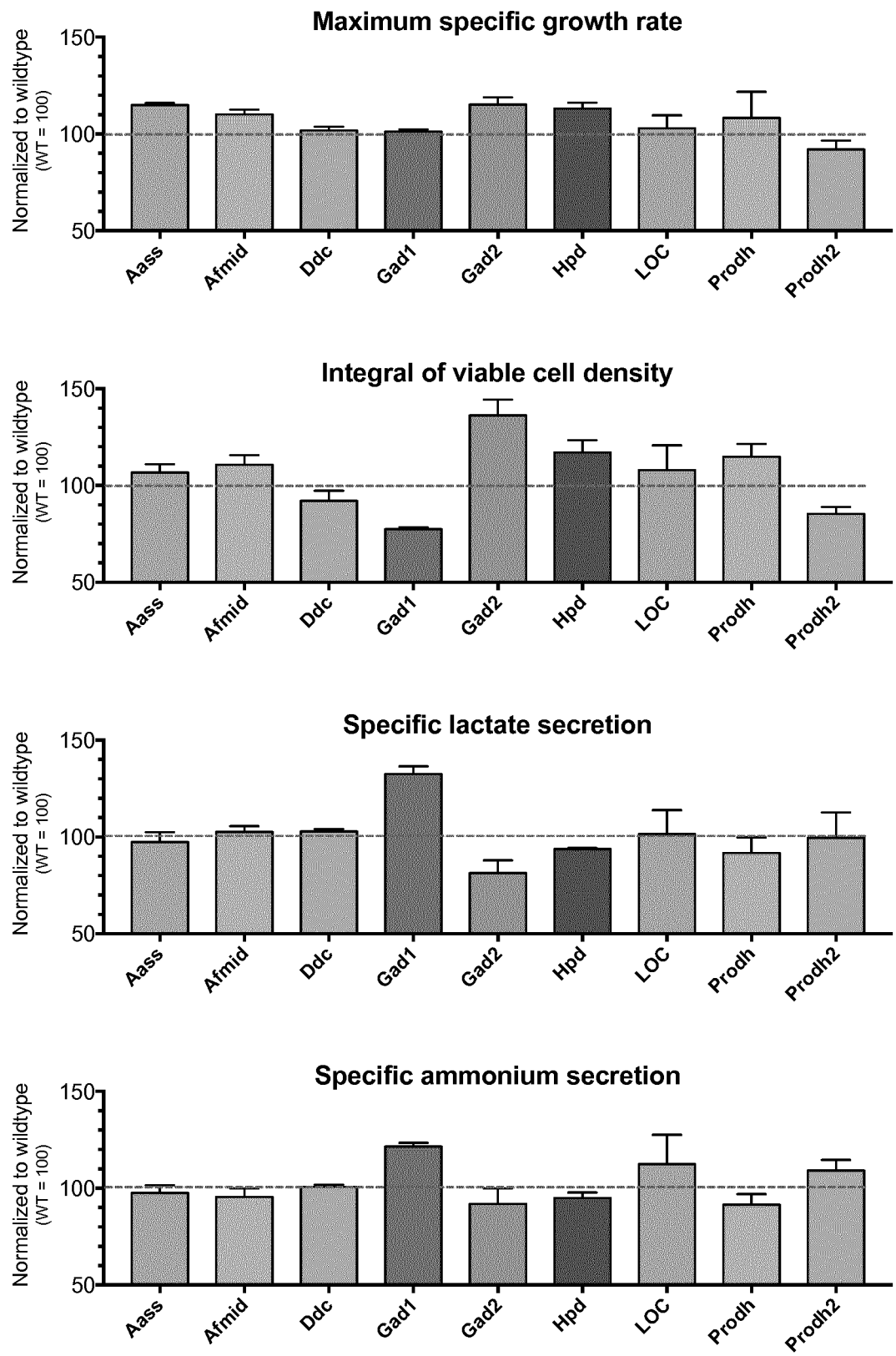

METHOD FOR REDUCING AMMONIUM AND LACTATE PRODUCTION IN CHO CELLS

FIELD OF THE INVENTION

The present invention relates to modified producer cells for improved production of therapeutic proteins. Specifically, the inventors have found that removing genes involved in amino acid catabolism in Chinese Hamster Ovary (CHO) cells improves the cell growth and viability and likely also the yield of a recombinant therapeutic protein produced by the cells.

BACKGROUND OF THE INVENTION

CHO cells are the predominant cell factory for production of recombinant therapeutic proteins, a segment of the pharmaceutical industry worth more than 140 billion USD in 2013 alone (Walsh, 2014). A central problem in CHO cell bioprocessing is accumulation of toxic metabolic by-products, which inhibit growth and impair product quality (Lao & Toth, 1997; Brodsky et al., 2014), leading to an overall reduced yield of high quality protein. CHO cells mainly acquire energy for growth and protein synthesis from glucose and glutamine catabolism, however evidence suggest that other amino acids are also commonly utilized as carbon source (Nicolae et al., 2014). Catabolism of amino acids is the main source of ammonium production in mammalian metabolism. The catabolic reaction involves a deamination step where the α-amino group is transferred to α-ketoglutarate to form glutamate, which is then oxidatively deaminated to yield an ammonium ion. Catabolism of amino acids is coupled to reduction of $NAD^+$ to produce NADH. Production of NADH in the cytosol has been shown to perturb the redox equilibrium, which force the cell to regenerate cytosolic NAD+ pools through lactate dehydrogenase activity to maintain redox homeostasis (Templeton et al., 2014). In this manner, catabolism of amino acids may indirectly increase lactate production in CHO cells.

Multiple toxic metabolites derived from amino acid catabolic pathways have been identified in mammalian cells. Among these are intermediates in the primary catabolic pathway of L-tryptophan, the kynurenine pathway: 3-hydroxykynurenine, 3-hydroxyanthranilic acid and 5-hydroxy-anthranilic acid (Sallée, 2014). Furthermore, toxic metabolites have been identified in catabolism of L-tyrosine, which are synthesized from L-phenylalanine and degraded into the following cytotoxic metabolites: 4-hydroxyphenylpyruvate, homogenisate, 4-maleyacetoacetate and fumarylacetate (Pan et al., 2013). Finally, reactive aldehydes produced in the catabolic pathway of L-lysine, the saccharopine pathway, are potentially toxic and can form adducts and condensation products with small molecules (e.g. amines), proteins and DNA (Hallen et al., 2013).

The present invention provides for methods for targeted disruption of amino acid catabolic pathways in CHO cells that cause an improved phenotype, with increased specific growth rate, increased biomass yield and reduced cell specific secretion of lactate and ammonium.

OBJECT OF THE INVENTION

It is an object of embodiments of the invention to provide mammalian cells, which cells has a phenotype with increased growth rate and/or increased biomass yield and/or speed of expression of an exogenous protein of interest.

It is an object of embodiments of the invention to provide mammalian cells, which cells has a phenotype with reduced specific secretion of lactate and/or reduced cell specific secretion of ammonium.

It is an object of embodiments of the invention to provide mammalian cells, which cells produce fewer amounts of toxic metabolites from amino acid catabolic pathways.

It is a further object of embodiments of the invention to provide mammalian cells, which has targeted inactivation of one or more endogenous genes involved in amino acid catabolism.

SUMMARY OF THE INVENTION

It has been found by the present inventor(s) that by knocking out genes involved in amino acid catabolism, the cells produce less toxic metabolites. This may be measured as e.g. reduced cell specific secretion of lactate and/or reduced cell specific secretion of ammonium. As a consequence of this disruption or downregulation of functional genes involved in amino acid catabolism the cells provides for an increased growth rate, increased biomass yield and/or speed of expression of an exogenous protein of interest.

So, in a first aspect the present invention relates to a recombinant mammalian cell having one or more endogenous genes involved in amino acid catabolism inactivated and/or down regulated.

In a second aspect the present invention relates to a recombinant mammalian cell having one or more endogenous genes involved in amino acid catabolism selected from the group consisting of Hpd, Ddc, Afmid, Aass, Prodh, Prodh2, Gad1, Gad2, and LOC100759874 inactivated and/or downregulated.

In a third aspect the present invention relates to a recombinant mammalian cell having one or more endogenous genes selected from the group consisting of Hpd, Ddc, Afmid, Aass, Prodh, Prodh2, Gad1, Gad2, and LOC100759874 inactivated and/or downregulated.

In a further aspect the present invention relates to a method of cell culturing comprising the growth of a population of recombinant mammalian cells according to the invention in a suitable cell culture medium and maintaining at least one metabolite from amino acid catabolism below a certain value. In some embodiments the metabolite is selected from ammonium and lactate. In some embodiments the metabolite, such as ammonium or lactate is kept at a level below a concentration of 3 mM as measured by assays described herein. In some embodiments the method comprises the step of measuring the concentration of the at least one metabolite, and, when the measured concentration is above a predefined value, the concentration of precursor of said at least one metabolite in the cell culture medium is decreased by reducing the amount of precursor provided to the cells. In some embodiments the maximum viable cell density of said population of recombinant mammalian cells is higher than $1\times10^6$ cells/ml, such as higher than $5\times10^6$ cells/ml, such as higher than $1\times10^7$ cells/ml, such as higher than $5\times10^7$ cells/ml, such as higher than $1\times10^8$ cells/ml, such as higher than $5\times10^8$ cells/ml, such as higher than $1\times10^9$ cells/ml.

In a further aspect the present invention the use of a cell according to the invention for the production of a recombinant exogenous protein of interest.

LEGENDS TO THE FIGURE

FIG. 1. Comparison of growth rate, integral of viable cell density and specific secretion levels of lactate and ammonium in cell lines with full or partial disruption of the following genes: Aass, Afmid, Ddc, Gad1, Gad2, Hpd, LOC100759874, Prodh and Prodh2. Values are normalized to a non-transfected control cell line. Error bars indicate standard deviation of biological triplicates.

DETAILED DISCLOSURE OF THE INVENTION

Definitions

The term "inactivated" as used herein refers to a gene that has been completely or partially disrupted, removed, or knocked out, to get an expression of said gene product downregulated or completely absent at a protein functional level.

The term "downregulated" as used herein refers to a gene, which expression has been lowered, diminished by some means, e.g. antisense, protein inactivators or by other means.

The term "mammalian cell" as used herein refers to any cell from or derived from any mammal (e.g. a human, a hamster, a mouse, a monkey, a rat, a pig, a cow, or a rabbit). In some embodiments, a mammalian cell can be an immortalized cell, such as an in vitro cell line. In some embodiments, the mammalian cell is a differentiated cell. In some embodiments, the mammalian cell is an undifferentiated cell. Recombinant mammalian cell refers to a cell being genetically modified in some way from the wild type parent cell.

The term "culturing" or "cell culturing" as used herein refers to the maintenance or growth of a mammalian cell under a controlled set of physical conditions.

Hpd refers to a gene normally described with a gene ID of 100768220 and a gene description name or synonyms such as 4-hydroxyphenylpyruvate dioxygenase, 4-hydroxyphenylpyruvic acid oxidase, 4HPPD, HPD, and HPPDase.

Ddc refers to a gene normally described with a gene ID of 100761742 and a gene description name or synonyms such as dopa decarboxylase (aromatic L-amino acid decarboxylase), Aromatic-L-amino-acid decarboxylase, and DOPA decarboxylase.

Afmid refers to a gene normally described with a gene ID of 100773211 and a gene description name or synonyms such as arylformamidase, Kynurenine formamidase, Arylformamidase, N-formylkynurenine formamidase, FKF, KFA, and Kfase.

Aass refers to a gene normally described with a gene ID of 100751161 and a gene description name or synonyms such as aminoadipate-semialdehyde synthase, Alpha-aminoadipic semialdehyde synthase, Lysine ketoglutarate reductase, Saccharopine dehydrogenase, LKR, LOR, and SDH.

Prodh refers to a gene normally described with a gene ID of 100750856 and a gene description name or synonyms such as proline dehydrogenase (oxidase) 1, Proline dehydrogenase 1, Proline oxidase, Proline oxidase 2, and p53-induced gene 6 protein.

Prodh2 refers to a gene normally described with a gene ID of 100773901 and a gene description name or synonyms such as proline dehydrogenase (oxidase) 2, Probable proline dehydrogenase 2, Kidney and liver proline oxidase 1, Probable proline oxidase 2, and HsPDX1.

Gad1 refers to a gene normally described with a gene ID of 100765882 and a gene description name or synonyms such as glutamate decarboxylase 1 (brain, 67 kDa), Glutamate decarboxylase 1, 67 kDa glutamic acid decarboxylase, Glutamate decarboxylase 67 kDa isoform, and GAD-67.

Gad2 refers to a gene normally described with a gene ID of 100757642 and a gene description name or synonyms such as glutamate decarboxylase 2 (pancreatic islets and brain, 65 kDa), Glutamate decarboxylase 2, 65 kDa glutamic acid decarboxylase, Glutamate decarboxylase 65 kDa isoform, and GAD-65.

LOC100759874 refers to a gene normally described with a gene ID of 100759874 and a gene description name or synonyms such as L-threonine 3-dehydrogenase and TDH.

The cells provided herein can be modified from a variety of different mammalian cells. The mammalian cell can be, e.g. a cell that grows in suspension or it can be an adherent cell. Non-limiting examples of mammalian cells used herein include: Chinese hamster ovary (CHO) cells, such as CHO-K1, Sp2.0, myeloma cells (e.g., NS/0), B-cells, hybridoma cells, T-cells, human embryonic kidney (HEK) cells (e.g, HEK293E, HEK293T, and HEK 293F), African green monkey kidney epithelial cells (Vero) cells, and Madin-Darby Canine (Cocker Spaniel) kidney epithelial cells (MDCK) cells. Additional mammalian cells that can be used according to the invention described herein are known in the art.

The mammalian cell can be modified to express an exogenous protein of interest, such as containing a recombinant nucleic acid (e.g., a nucleic acid stably integrated in the mammalian cell's genome) that encodes a recombinant protein, such as a therapeutic protein. Non-limiting examples of exemplary recombinant proteins are described below.

A nucleic acid encoding a recombinant protein can be introduced into a mammalian cell using a wide variety of methods known in molecular biology and molecular genetics. Non-limiting examples include transfection (e.g., lipofection), transduction (e.g., lentivirus, adenovirus, or retrovirus infection), and electroporation. In some instances, the nucleic acid that encodes a recombinant protein is not stably integrated into a chromosome of the mammalian cell (transient transfection); while in others the nucleic acid is integrated. Alternatively or in addition, the nucleic acid encoding a recombinant protein can be present in a plasmid and/or in a mammalian artificial chromosome (e.g., a human artificial chromosome). Alternatively or in addition, the nucleic acid can be introduced into the cell using a viral vector (e.g., a lentivirus, retrovirus, or adenovirus vector). The nucleic acid can be operably linked to a promoter sequence (e.g., a strong promoter, such as a β-actin promoter and CMV promoter, or an inducible promoter). A selection system may also be applied, such as by use of a selectable marker (e.g., dihydrofolate reductase (DHFR) selection system, a system based on the selection of the glutamine synthetase (GS) gene, or a gene that confers hygromycin, puromycin, or neomycin resistance to the mammalian cell).

In some instances, the recombinant protein is a secreted protein and is released by the mammalian cell into the extracellular medium (e.g., the first and/or second liquid culture medium). For example, a nucleic acid sequence encoding a soluble recombinant protein can contain a sequence that encodes a secretion signal peptide at the N- or C-terminus of the recombinant protein, which is cleaved by an enzyme present in the mammalian cell, and subsequently released into the extracellular medium (e.g., the first and/or second liquid culture medium). For example, such a secreted recombinant protein can be a secreted immunoglobulin, a secreted enzyme, a secreted growth factor, a secreted protein fragment, or a secreted engineered protein. In other instances, the recombinant protein is a soluble protein that is not secreted, and the recombinant protein is recovered from within the mammalian cell. For example, a recombinant protein that is not secreted can be an immunoglobulin, an enzyme, a growth factor, a protein fragment, or an engineered protein.

Non-limiting examples of recombinant proteins that can be produced by the methods provided herein include immunoglobulins (including light and heavy chain immunoglobulins, antibodies, or antibody fragments (e.g., any of the antibody fragments described herein), enzymes (e.g., a galactosidase (e.g., an alpha-galactosidase), Myozyme, or Cerezyme), proteins (e.g., a growth factor, human erythropoietin, tumor necrosis factor (TNF), or an interferon alpha or beta), an engineered protein, or immunogenic or antigenic proteins or protein fragments (e.g., proteins for use in a vaccine). In some embodiments, the recombinant protein is an engineered antigen-binding polypeptide that contains at least one multifunctional recombinant protein scaffold (see, e.g., the recombinant antigen-binding proteins described in Gebauer et al, Current Opin. Chem. Biol. 13:245-255, 2009; and U.S. Patent Application Publication No. 2012/0164066. Non-limiting examples of recombinant proteins that are antibodies include: panitumumab, omalizumab, abagovomab, abciximab, actoxumab, adalimumab, adecatumumab, afelimomab, afutuzumab, alacizumab, alacizumab, alemtuzumab, alirocumab, altumomab, amatuximab, anatumomab, apolizumab, atinumab, tocilizumab, basilizimab, bectumomab, belimumab, bevacizumab, biciromab, canakinumab, cetuximab, daclizumab, densumab, eculizumab, edrecolomab, efalizumab, efungumab, ertumaxomab, etaracizumab, golimumab, infliximab, natalizumab, palivizumab, panitumumab, pertuzumab, ranibizumab, rituximab, tocilizumab, and trastuzumab. Additional examples of therapeutic antibodies that can be produced by the methods described herein are known in the art. Additional non-limiting examples of recombinant proteins that can be produced by the present methods include: alglucosidase alfa, laronidase, abatacept, galsulfase, lutropin alfa, antihemophilic factor, agalsidase beta, interferon beta-1a, darbepoetin alfa, tenecteplase, etanercept, coagulation factor IX, follicle stimulating hormone, interferon beta-la, imiglucerase, dornase alfa, epoetin alfa, and alteplase.

The methods for inactivation, such as the complete or partial disruption, removal of a gene involved in amino acid catabolism is known to the person skilled in the art. Relevant genes may be knocked out to get an expression of said gene downregulated or completely absent. Suitable methods include RNA interference with antisense RNA, antisense DNA, a Ribozyme, inhibitors of the gene transcription or an inhibitor of the relevant gene products.

Complete or partial gene knock out may be accomplished by the use of Clustered Regularly Interspaced Short Palindromic Repeats (CRISPR)-Cas9, Zinc finger (ZF) approach, TALENs or similar methods. Thus, genes involved in amino acid catabolism (e.g. Hpd, Ddc, Afmid, Aass, Prodh, Prodh2, Gad1, Gad2, and LOC100759874) may be inactivated and/or downregulated in a cell, by use of methods comprising genome perturbation, gene-editing and/or gene disruption capability such as with nucleic acid vector systems related to CRISPR and components thereof, nucleic acid vector systems encoding fusion proteins comprising zinc finger DNA-binding domains (ZF) and at least one cleavage domain or at least one cleavage half-domain (ZFN) and/or nucleic acid vector systems encoding a first transcription activator-like (TAL) effector endonuclease monomer and a nucleic acid encoding a second cleavage domain or at least one cleavage half-domain (TALEN).

In some embodiments relevant genes are inactivated and/or downregulated by using CRISPR/Cas9.

Embodiments of the Invention

As described above in some aspects the present invention relates to a recombinant mammalian cell having one or more endogenous genes involved in amino acid catabolism selected from the group consisting of Hpd, Ddc, Afmid, Aass, Prodh, Prodh2, Gad1, Gad2, and LOC100759874 inactivated and/or downregulated.

In some embodiments the cells according to the inventions has a phenotype with increased specific growth rate as compared to the corresponding cell without said one or more gene inactivated and/or downregulated.

In some embodiments the cells according to the inventions has a phenotype with increased biomass yield and/or speed of expression of an exogenous protein of interest; as compared to the corresponding cell without said one or more gene inactivated and/or downregulated.

In some embodiments the cells according to the inventions has a phenotype with reduced cell specific secretion of lactate as compared to the corresponding cell without said one or more gene inactivated and/or downregulated.

In some embodiments the cells according to the inventions has a phenotype with reduced cell specific secretion of ammonium as compared to the corresponding cell without said one or more gene inactivated and/or downregulated.

In some embodiments the cells according to the inventions is selected from the group consisting of a Chinese Hamster Ovarian (CHO) cells, such as CHO-K1; Baby Hamster Kidney (BHK) cell; COS cell; HEK293; NS0; SP2/0; YB2/0; HUVEC; HKB; PER-C6; or derivatives of any of these cells.

It is to be understood that a derivative of any particular cell line, is a cell line that is a variant of the original cell line from which it is derived. A cell line derivate may be changed from the original cell line by the addition, deletion, inactivation or other modification of one or more endogenous genes.

In some embodiments the cells according to the inventions has been further modified to express an exogenous protein of interest, such as therapeutic protein.

In some embodiments the cells according to the inventions expresses a protein of interest selected from a glycosylated protein, such as a monoclonal antibody, granulocyte colony stimulating factor, interferon-alpha, interferon-beta, Factor VIIa, Factor IX, follicle stimulating hormone, erythropoietin, granulocyte macrophage colony stimulating factor, interferon-gamma, alpha-1-protease inhibitor, beta-glucosidase, tissue plasminogen activator protein, interleukin-2, Factor VIII, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNase, chimeric anti-tumor necrosis factor antibody, human insulin, hepatitis B sAg, and human growth hormone.

In some embodiments the cells according to the inventions has a specific lactate secretion rate decreased by more than 1%, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30% as compared to the corresponding cell without said one or more gene inactivated and/or downregulated.

In some embodiments the cells according to the inventions has a specific ammonium secretion rate decreased by more than 1%, such as 2, 3, 4, 5, 6, 7, 8, 9, 10, 11, 12, 13, 14, 15, 16, 17, 18, 19, 20, 21, 22, 23, 24, 25, 26, 27, 28, 29, or 30% as compared to the corresponding cell without said one or more gene inactivated and/or downregulated.

In some embodiments the cells according to the inventions has two or more, such as three, four, five, six, seven, eight, or nine genes selected from the group consisting of Hpd, Ddc, Afmid, Aass, Prodh, Prodh2, Gad1, Gad2, and LOC100759874 inactivated and/or downregulated.

EXAMPLE 1

Metabolic Network Reconstruction

A draft network reconstruction of the glycolytic and amino acid catabolic pathways in CHO cells was generated using the mouse metabolic pathways as template. Biochemical pathway data from mouse metabolism was retrieved from the Kyoto Encyclopedia of Genes and Genomes database (Kanehisa and Goto, 2000; Kanehisa et al., 2014) and homologous gene sequences in the CHO genome were identified using the Chinese hamster genome database www.CHOgenome.org (Hammond et al., 2012). The draft network reconstruction was further refined by careful curation of gene-protein-reaction relationships using manual genome annotation and literature evidence. The finalized reconstruction featured 319 proteins catalyzing 183 reactions with 188 metabolites.

Single-Guide RNA Target Design and Transfection

Design and selection of single-guide RNA (sgRNA) target sites was performed with the online tool "CRISPy" (Ronda et al., 2014). The sgRNA expression vectors were constructed as previously described (Ronda et al., 2014). Prior to transfection, CHO-S suspension cells obtained from Life Technologies were grown in CD-CHO medium supplemented with 8 mM L-glutamine (Gibco) and 0.5% anti-clumping reagent (Gibco) in a humidified shaking incubator operated at 37° C., 5% CO2 and 120 rpm. One day prior to transfection, cells were washed and seeded in medium without anti-clumping reagent at $5 \times 10^5$ cells/mL. Cells were transfected with expression vectors encoding GFP_2A-Cas9 (Gray et al., 2015) and sgRNA targeting Aass, Afmid, Ddc, Gad1, Gad2, Hpd, LOC100759874, Prodh and Prodh2 individually, to generate single-gene knock out transfectants. For each sample, cell cultures with cell density of $1 \times 10^6$ cells/mL in 125 mL shake flasks (Corning), were transfected with 17.7 µg DNA using FreeStyle™ MAX reagent together with OptiPRO SFM medium (Life Technologies), according to the manufacturers recommendations. Anti-clumping reagent (0.5%) was added one day after transfection. Enrichment and isolation of transfected cells, as well as deep sequencing analysis of clone genotypes, were performed as previously described (Gray et al., 2015).

Cell Culture

Cultures were initiated from cryopreserved vials in preheated CD-CHO medium (Thermo Fisher Scientific) supplemented with 8 mM L-glutamine (Gibco) and 0.5% anti-clumping reagent (Gibco). Cell culture was performed in 250 mL vented Erlenmeyer shake flasks (Corning, N.Y., USA) with a working volume of 80 mL in a humidified shaking incubator operated at 37° C., 5% CO2 and 120 rpm. All cultures were seeded at $3 \times 10^5$ cells/mL and grown for 6 days in batch culture mode. Samples were drawn on a daily basis and analyzed for cell density and viability using Nucleocounter NC-200 (Chemometec, Denmark). Extracted culture supernatants were analyzed for glucose, lactate, glutamine, glutamate and ammonium using BioProfile 400 Plus (Nova Biomedical, Waltham, Mass., USA).

Calculations and Statistics

Maximum specific growth rate was calculated using exponential regression of viable cell density from day 0 to day 3. Average specific production rates of lactate and ammonium were calculated during the time interval from day 0 to day 3, by dividing the increase in metabolite concentration by the increase in integral of viable cell density (IVCD). The statistical test for determination of physiological differences between clone populations was performed using Student's t-test with a significance level of $\alpha=0.05$.

Results and Discussion

Selection of Target Amino Acid Catabolic Genes for Gene Editing

The selection of target genes for knockout was guided by integrating differential gene expression data in the metabolic network reconstruction of amino acid catabolism. The differential gene expression dataset was generated from an IgG producing cell line and a non-producing cell line (Lund et al, 2017). Thus, the dataset is assumed to reflect changes in gene expression levels as a direct response to the metabolic burden of recombinant protein production. Interestingly, we observed a general upregulation of glycolytic genes, indicating increased catabolism of glucose to meet the metabolic demand from recombinant protein synthesis. When inspecting the gene expression levels in amino acid catabolic pathways, we found that the L-tryptophan, L-lysine, L-phenylalanine and L-tyrosine pathways were upregulated in the protein producing cell line relative to the non-producing cell line, indicating that CHO cells increase catabolism of said amino acids when producing recombinant proteins. Therefore, in order to restrict the catabolism of L-tryptophan, L-lysine, L-phenylalanine and L-tyrosine we selected the following genes, encoding catabolic enzymes, for knockout: Afmid, Aass, Ddc and Hpd. In addition to these genes, we selected a second set of genes encoding decarboxylases and dehydrogenases for knockout, as they were expected to reduce specific secretion of lactate and ammonium: Gad1, Gad2, Prodh, Prodh2 and LOC100759874.

Knockout of amino acid catabolic genes improves growth and integral of viable cell density and reduce specific lactate and ammonium secretion.

The effect of gene disruptions showed increased maximum specific growth rate in eight of nine clones, except for the clone with gene Prodh2 disrupted, which had a negative impact on maximum specific growth rate. Of the eight gene disruptions with positive effect on maximum specific growth rate, we found that Aass, Afmid, Gad2 and Hpd grew significantly faster (Student's t-test, p-value<0.05). The integral of viable cell density (IVCD) is an important process parameter, as it represents the cell-work-hours available for protein synthesis and is correlated to overall process protein titer. We found that six of nine gene disruptions improved IVCD and Afmid, Gad2, Hpd and Prodh were significantly improved (Student's t-test, p-value<0.05). For specific secretion rate of lactate and ammonium, we found that four of eight clones showed reduced lactate secretion rate, while five clones had reduced ammonium secretion rate. From these clones, we found that specific lactate secretion rate was significantly reduced in clones with Gad2 and Hpd disrupted (Student's t-test, p-value<0.05), while only the clone with Hpd disrupted had significantly reduced specific ammonium secretion rate. However, both disruptions of Afmid and Gad2, produced were near significantly reduced secretion rates of ammonium with p-values of 0.08. In conclusion, we provide evidence that targeted gene disruptions in amino acid catabolism can improve critical process parameters for therapeutic protein production. Specifically, we demonstrated that disrupting Hpd and Gad2 increases maximum specific growth rate and IVCD, while reducing specific secretion of lactate and ammonium.

EXAMPLE 2

Knock Out of HPD in a IgG-Producing Cell Line

Single-Guide RNA Target Design and Transfection

Design and selection of single-guide RNA (sgRNA) target sites was performed with the online tool "CRISPy" (Ronda et al., 2014). The sgRNA expression vectors were constructed as previously described (Ronda et al., 2014). Prior to transfection, CHO-S suspension cells obtained from Life Technologies, transformed to express an IgG and selected for high specific productivities, were grown in CD-CHO medium supplemented with 8 mM L-glutamine (Gibco) and 0.5% anti-clumping reagent (Gibco) in a humidified shaking incubator operated at 37° C., 5% CO2 and 120 rpm. One day prior to transfection, cells were washed and seeded in medium without anti-clumping reagent at $5 \times 10^5$ cells/mL. Cells were transfected with expression vectors encoding GFP_2A-Cas9 (Gray et al., 2015) and sgRNA targeting Gad2 to generate single-gene knock out transfectants. For controls, "mock" cell lines were generated transfected with a vector encoding GFP_2A-Cas9 and no sgRNA. For each sample, cell cultures with cell density of $1 \times 10^6$ cells/mL in 125 mL shake flasks (Corning), were transfected with 17.7 µg DNA using FreeStyle™ MAX reagent together with OptiPRO SFM medium (Life Technologies), according to the manufacturers recommendations. Anti-clumping reagent (0.5%) was added one day after transfection. Enrichment and isolation of transfected cells, as well as deep sequencing analysis of clone genotypes, were performed as previously described (Gray et al., 2015).

Cell Culture

Cultures were initiated from cryopreserved vials in pre-heated CD-CHO medium (Thermo Fisher Scientific) supplemented with 8 mM L-glutamine (Gibco) and 0.5% anti-clumping reagent (Gibco). Cell culture was performed in 250 mL vented Erlenmeyer shake flasks (Corning, N.Y., USA) with a working volume of 80 mL in a humidified shaking incubator operated at 37° C., 5% CO2 and 120 rpm. All cultures were seeded at $3 \times 10^5$ cells/mL and grown for 7 days in batch culture mode. Samples were drawn on a daily basis and analyzed for cell density and viability using Nucleocounter NC-200 (Chemometec, Denmark). Extracted culture supernatants were analyzed for glucose, lactate, glutamine, glutamate and ammonium using BioProfile 400 Plus (Nova Biomedical, Waltham, Mass., USA). IgG quantification was assessed using an Octet biosensor (Pall ForteBio, Portsmouth, United Kingdom)

Calculations

Maximum specific growth rate was calculated using exponential regression of viable cell density from day 0 to day 3. Average specific production rates of lactate and ammonium were calculated during the time interval from day 0 to day 3, by dividing the increase in metabolite concentration by the increase in integral of viable cell density (IVCD). Specific productivities of IgG was calculated from day 0 to day 3 by dividing the increase in IgG titer by the increase in IVCD.

Results

A Hpd-knockout clone and a control clone transfected with a mock Cas9-plasmid were both derived from a IgG-producing cell line. Cells were cultured in shake flasks and cell, metabolite, and IgG concentrations were measured daily. Growth characteristics and productivities are presented in TABLE 1.

TABLE 1

PERFORMANCE INDICATORS FOR IgG PRODUCING CELL LINES

|  | Control | ΔHpd |
|---|---|---|
| $\mu_{max}$ (Relative, control index 100) | 100 | 101 |
| $q_{Lac}$, day 3 (Relative, control index 100) | 100 | 70 |
| $q_{NH3}$, day 3 (Relative, control index 100) | 100 | 87 |
| IVCD, day 6 (Relative, control index 100) | 100 | 118 |
| Titer, day 6 (relative, Control index 100) | 100 | 138 |
| $q_p$, day 3 (Relative, Control index 100) | 100 | 101 |

When compared to the control, the ΔHpd cell line performs markedly better, having lower productivities of ammonium and lactate, and higher IVCD. The $q_p$ is similar in the two cell lines, but the higher IVCD results in a higher final titer.

LIST OF REFERENCES

Brodsky A N, Caldwell M, Bae S, Harcum S W, 2014, Glycosylation-related genes in NS0 cells are insensitive to moderately elevated ammonium concentrations, Journal of Biotechnology, 187 p.78-86.

Gray L M, Lee J S, Gerling S, Kallehauge T B, Hansen A H, Kol S, Lee G M, Pedersen L E, Kildegaard H F. 2015. One-step generation of triple knockout CHO cell lines using CRISPR/Cas9 and fluorescent enrichment. Biotechnology Journal, 10(9):1446-1456.

Hallen A, Jamie J F, Cooper A J L, 2013, Lysine metabolism in mammalian brain: an update on the importance of recent discoveries, Amino Acids 45: p. 1249-1272.

Hammond S, Kaplarevic M, Borth N, Betenbaugh M J, Lee K H. 2012. Chinese hamster genome database: An online resource for the cho community at www.CHOgenome.org. Biotechnol Bioeng 109:1353-1356.

Kanehisa M, Goto S. 2000. KEGG: Kyoto encyclopedia of genes and genomes. Nucleic Acids Res 28(1):27-30.

Lao M S, & Toth D, 1997, Effects of ammonium and lactate on growth and metabolism of a recombinant Chinese hamster ovary cell culture, Biotechnology progress, 13:5 p.688-91.

Lund A M, Kaas C S, Brandl J, Pedersen L E, Kildegaard H F, Kristensen C, Andersen M R. 2017. Network reconstruction of the mouse secretory pathway applied on CHO cell transcriptome data. BMC Syst Biol. 11(1):37.

Nicolae A, Wahrheit J, Bahnemann J, Zeng A, Heinzle E, 2014, Non-stationary 13C metabolic flux analysis of Chinese hamster ovary cells in batch culture using extracellular labeling highlights metabolic reversibility and compartmentalization, BMC Systems Biology, 8:50 p.1-15.

Pan Y S, Zhang Y, Cui J, Liu Y, McAllan B M, Liao C C, Zhang S, 2013, Adaptation of phenylanaline and tyrosine catabolic pathway to hibernation in bats, PLoS ONE 8(4): e62039. doi:10.1371/journal.pone.0062039

Ronda C, Pedersen L E, Hansen H G, Kallehauge T B, Betenbaugh M J, Nielsen A T, Kildegaard H F. 2014. Accelerating genome editing in CHO cells using CRISPR Cas9 and CRISPy, a web-based target finding tool. Biotechnol. Bioeng., 111:1604-1616.

Sallée M, Dou L, Cerini C, Poitevin S, Brunet P, Burtey S, 2014, They aryl hydrocarbon receptor-activating effect of uremic toxins from tryptophan metabolism: A new concept to understand cardiovascular complications of chronic kidney disease, Toxins, 6:3 p.934-949.

Templeton N, Lewis A, Dorai H, Qian E A, Campbell M P, Smith K D, Lang S E, Betenbaugh M J, Young J D, 2014, The impact of anti-apoptotic gene Blc-2 expression on CHO central metabolism, Metabolic engineering, 25 p.92-102.

Walsh G, 2014, Biopharmaceutical benchmarks 2014, Nature biotechnology, 32:10 p.992-1000.

The invention claimed is:

1. A recombinant Chinese Hamster Ovarian (CHO) cell having one or more endogenous genes involved in amino acid catabolism selected from the group consisting of 4-hydroxyphenylpyruvate dioxygenase (Hpd), dopa decarboxylase (Ddc), arylformamidase (Afmid), aminoadipate-semialdehyde synthase (Aass), Proline dehydrogenase 1 (Prodh), Proline dehydrogenase 2 (Prodh2), glutamate decarboxylase 1 (Gad1), glutamate decarboxylase 2 (Gad2), and L-threonine 3-dehydrogenase (LOC100759874) inactivated and/or downregulated.

2. The recombinant CHO cell according to claim 1, having a phenotype with increased specific growth rate as compared to the corresponding cell without said one or more gene inactivated and/or downregulated.

3. The recombinant CHO cell according to claim 1, having a phenotype with increased biomass yield and/or speed of expression of an exogenous protein of interest; as compared to the corresponding cell without said one or more gene inactivated and/or downregulated.

4. The recombinant CHO cell according to claim 1, having a phenotype with reduced cell specific secretion of lactate as compared to the corresponding cell without said one or more gene inactivated and/or downregulated.

5. The recombinant CHO cell according to claim 1, having a phenotype with reduced cell specific secretion of ammonium as compared to the corresponding cell without said one or more gene inactivated and/or downregulated.

6. The recombinant CHO cell according to claim 1, where the cell has been further modified to express an exogenous protein of interest.

7. The recombinant CHO cell according to claim 6, where the cell expresses a protein of interest selected from a glycosylated protein, a monoclonal antibody, granulocyte colony stimulating factor, interferon-alpha, interferon-beta, Factor VIIa, Factor IX, follicle stimulating hormone, erythropoietin, granulocyte macrophage colony stimulating factor, interferon-gamma, alpha-1-protease inhibitor, beta-glucosidase, tissue plasminogen activator protein, interleukin-2, Factor VIII, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNase, chimeric anti-tumor necrosis factor antibody, human insulin, hepatitis B sAg, and human growth hormone.

8. The recombinant CHO cell according to claim 1, which cell has a specific lactate secretion rate decreased by more than 1% as compared to the corresponding cell without said one or more gene inactivated and/or downregulated.

9. The recombinant CHO cell according to claim 1, which cell has a specific ammonium secretion rate decreased by more than 1% as compared to the corresponding cell without said one or more gene inactivated and/or downregulated.

10. The recombinant CHO cell according to claim 1, which cell has two or more genes selected from the group consisting of Hpd, Ddc, Afmid, Aass, Prodh, Prodh2, Gad1, Gad2, and LOC100759874 inactivated and/or downregulated.

11. A method of cell culturing comprising the growing a population of recombinant CHO cells according to claim 1 in a suitable cell culture medium and maintaining at least one metabolite selected from ammonium and lactate at a level below a concentration of 3 mM.

12. The method according to claim 11, which method comprises the step of measuring the concentration of said at least one metabolite, and, when the measured concentration is above 3 mM, the concentration of precursor of said at least one metabolite in the cell culture medium is decreased by reducing the amount of precursor provided to the cells.

13. The method according to claim 11, wherein the maximum viable cell density of said population of recombinant mammalian cells is higher than $1 \times 10^6$ cells/ml.

14. A method for producing a recombinant exogenous protein of interest, which method comprises culturing a cell as defined in claim 1 modified to express the exogenous protein of interest.

* * * * *